(12) United States Patent
Campbell et al.

(10) Patent No.: US 7,584,550 B2
(45) Date of Patent: Sep. 8, 2009

(54) APPARATUS AND METHOD FOR MEASURING WAVINESS OF SHEET MATERIALS

(75) Inventors: Edgar Robert Campbell, Hartsville, SC (US); Robert Shean Cumbee, Hartsville, SC (US); Jeffrey Thomas Moffat, Hartsville, SC (US)

(73) Assignee: Sonoco Development, Inc., Hartsville, SC (US)

(*) Notice: Subject to any disclaimer, the term of this patent is extended or adjusted under 35 U.S.C. 154(b) by 239 days.

(21) Appl. No.: 11/616,393

(22) Filed: Dec. 27, 2006

(65) Prior Publication Data

US 2008/0155850 A1 Jul. 3, 2008

(51) Int. Cl.
*G01B 5/00* (2006.01)

(52) U.S. Cl. .......................... 33/806; 33/533

(58) Field of Classification Search .......... 33/806, 33/533, 1 V, 1 BB, 832–833, 679.1, 549, 33/551–555; 73/788, 790, 818, 159, 866
See application file for complete search history.

(56) References Cited

U.S. PATENT DOCUMENTS

| | | | |
|---|---|---|---|
| 2,704,453 A | | 3/1955 | Davis |
| 3,298,605 A | * | 1/1967 | Bucke et al. ............... 33/556 |
| 3,411,075 A | | 11/1968 | Kahoun |
| 3,470,739 A | | 10/1969 | Takafuji et al. |
| 4,092,068 A | | 5/1978 | Lucas et al. |
| 4,417,351 A | * | 11/1983 | Williamson et al. ........ 33/679.1 |
| 4,500,607 A | | 2/1985 | Louden et al. |
| 4,574,493 A | * | 3/1986 | Woolsey ..................... 33/501 |
| 4,785,731 A | * | 11/1988 | Nguyen ..................... 702/166 |
| 4,790,525 A | * | 12/1988 | Mitzel et al. ................ 271/97 |
| 4,977,685 A | | 12/1990 | Shahlapour |
| 5,205,046 A | | 4/1993 | Barnett et al. |
| 5,235,988 A | * | 8/1993 | Johnson et al. ............... 33/836 |
| 5,471,762 A | | 12/1995 | Miller et al. |
| 5,678,447 A | | 10/1997 | Graff |
| 5,684,707 A | | 11/1997 | Rogowski |

(Continued)

FOREIGN PATENT DOCUMENTS

JP 59 145915 8/1984

OTHER PUBLICATIONS

The European Search Report for European Application No. 07254789.6; Filed Dec. 12, 2007; Date of Completion Apr. 23, 2008.

*Primary Examiner*—Yaritza Guadalupe-McCall
(74) *Attorney, Agent, or Firm*—Alston & Bird LLP

(57) ABSTRACT

A device and a method for measuring and quantifying waviness of sheet materials such as paper. The device in accordance with one embodiment comprises a base having a planar, smooth, and level upper surface for supporting a stack of sheets thereon, a plate-shaped weight for placing atop the stack of sheets, and a measuring device for measuring a vertical distance between a datum surface defined by the weight and a datum surface defined by the base. The measured distance is an indication of the height of the stack. In a preferred embodiment, the device also includes a programmed processor operable to calculate a "Wavy Ratio" based on the measured actual height H of the stack and a calculated "ideal" height of the stack, as Wavy Ratio=$H/(n \cdot t)$, where n is the number of sheets and t is the average caliper of the sheets.

18 Claims, 3 Drawing Sheets

U.S. PATENT DOCUMENTS

| | | |
|---|---|---|
| 6,219,141 B1 | 4/2001 | Perrault |
| 6,662,456 B1 * | 12/2003 | Triplett .................. 33/203 |
| 6,711,828 B2 | 3/2004 | McCune et al. |
| 7,335,280 B2 * | 2/2008 | Lampi et al. .................. 33/533 |
| 7,380,451 B2 * | 6/2008 | Kawasaki et al. ............. 73/159 |
| 2002/0083607 A1 * | 7/2002 | Atsuhiko et al. .............. 33/553 |
| 2003/0101608 A1 | 6/2003 | McCune et al. |

* cited by examiner

APPARATUS AND METHOD FOR MEASURING WAVINESS OF SHEET MATERIALS

BACKGROUND OF THE INVENTION

The invention relates to paper manufacture, and particularly to the manufacture of paper from recycled furnish.

Recycled paper is particularly susceptible to the development of "waves" in the paper, which typically extend in the machine direction but sometimes also extend in the cross-machine direction. Desirably, the paper should lay flat without ridges or waves. The degree to which the paper deviates from this ideal flat condition can vary, and sometimes the deviation is great enough to cause the paper to be unsuitable for its intended use. Currently, however, there is no known commercially available device that is relatively inexpensive, that is simple to use, and that can measure and quantify the "waviness" of paper. Instead, the waviness typically is subjectively evaluated by a person touching and feeling a sample of the paper. Such subjective evaluation obviously is subject to problems with regard to accuracy, repeatability, and standardization.

BRIEF SUMMARY OF THE INVENTION

The invention aims to develop a device and method for measuring and quantifying waviness of sheet materials such as paper. The device in accordance with one embodiment comprises a base having a planar, smooth, and level upper surface for supporting a stack of sheets thereon, a weight for placing atop the stack of sheets, and a measuring device for measuring a vertical distance between an upper datum plane corresponding to a top surface of the stack and a lower datum plane corresponding to a lower surface of the stack. The measured vertical distance is an indication of the height H of the stack.

In a preferred embodiment, the device also includes a programmed processor operable to calculate a "Wavy Ratio" based on the measured actual height of the stack and a calculated "ideal" height of the stack. If the sheets were perfectly flat, then the ideal height of a stack of n sheets would be n times the average caliper or thickness t of the sheets. Waviness will make the height of the stack greater than this ideal height. The wavy ratio is the ratio of the measured height H of the stack to the ideal height:

Wavy Ratio=$H/(n \cdot t)$.

Thus, generally the Wavy Ratio will be greater than 1.0.

The stack height H can be measured in various ways. In one embodiment, a ruler or graduated scale is fixed relative to the base such that the ruler is adjacent one edge of the weight atop the stack. The "zero" on the ruler is set at the same vertical level as the upper surface (i.e., the lower datum plane) of the base, which defines the lower surface of the stack. The location of the lower surface of the weight (i.e., the upper datum plane, which defines the top surface of the stack) on the ruler is an indication of the height H. Alternatively, the location of the upper surface of the weight on the ruler can be determined and the thickness of the weight (i.e., the vertical distance between the upper and lower surfaces of the weight) can be subtracted from the measured vertical distance to derive the height H.

Preferably, the height H is based on an average of a plurality of measurements taken with the stack in different rotational orientations about a vertical axis. This helps to account for any unevenness in the height of the stack. Advantageously, the paper samples all have their machine direction oriented in the same direction, and the stack is rotated as a unit about the vertical axis for the different measurements. For example, two measurements can be taken and averaged to derive the height H. The second measurement is taken after the stack is rotated 180° about the vertical axis relative to the first measurement.

The weight in one embodiment comprises a rectangular or square plate. The weight preferably has approximately the same length and width dimensions as the base. The apparatus can include vertical guide members for properly locating the weight directly above the base. In one embodiment, there are four vertical guide members that extend through apertures in the weight adjacent the corners of the weight.

A method of quality control for a sheet material in accordance with one embodiment of the invention comprises the steps of stacking a plurality n of sheets of the sheet material one upon another to form a stack, the sheets having an average caliper t; measuring a height H of the stack; determining a Wavy Ratio as Wavy Ratio=$H/(n \cdot t)$; and comparing the Wavy Ratio to a predetermined threshold value and rejecting the sheet material if the Wavy Ratio exceeds the threshold value. Alternatively, instead of computing a Wavy Ratio, an average effective caliper of the sheets can be computed as $t_{eff}=H/n$, and the method can comprise comparing the average effective caliper $t_{eff}$ to the average caliper t of the sheets and rejecting the sheet material if the average effective caliper $t_{eff}$ exceeds the average caliper t by more than a predetermined threshold value.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
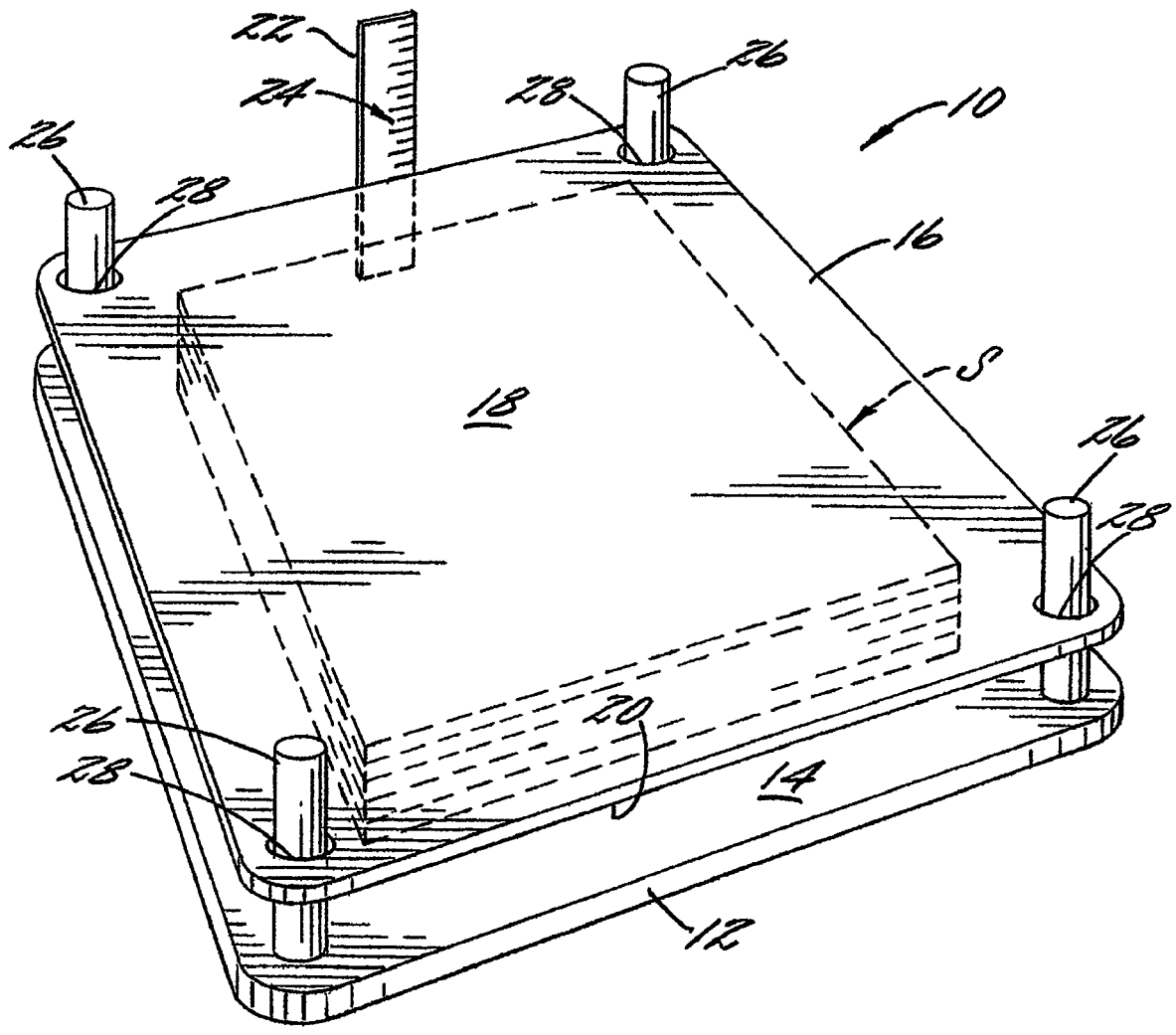
FIG. 1 is a perspective view of a testing apparatus in accordance with one embodiment of the invention.
Figure 2:
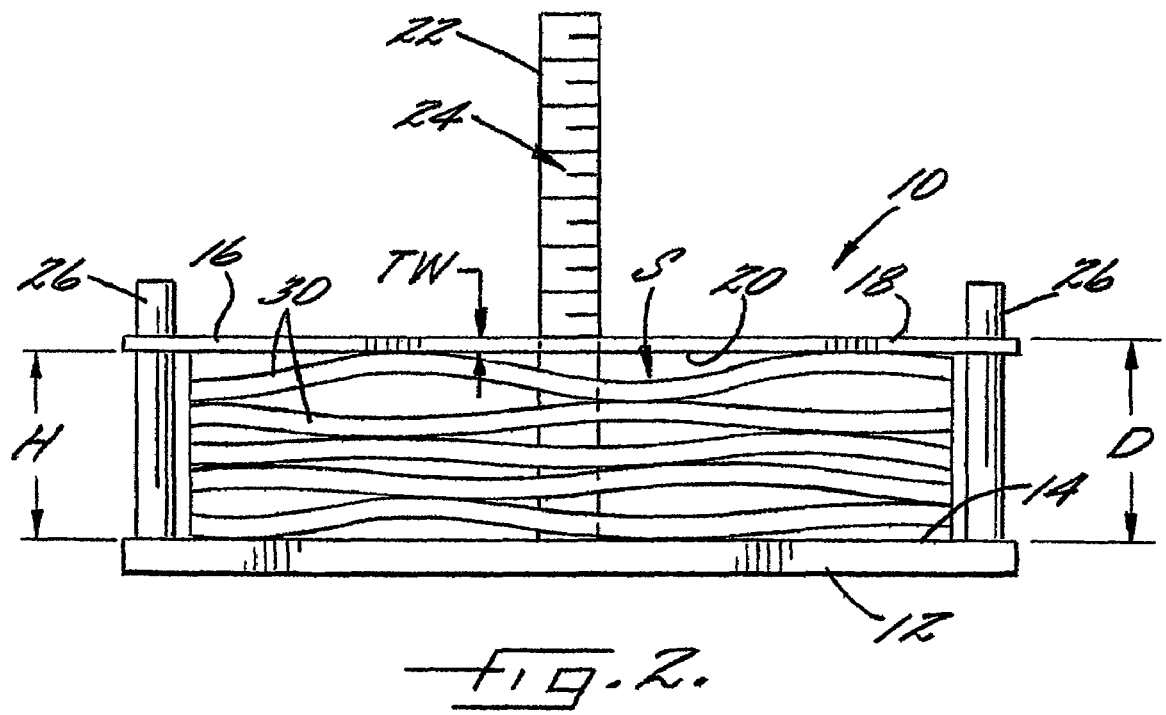
FIG. 2 is a diagrammatic front elevation of the testing apparatus, shown being used with a stack of sheets whose waviness is illustrated in greatly exaggerated fashion for clarity of illustration.

A testing apparatus 10 in accordance with one embodiment of the invention is shown in FIGS. 1 and 2. The apparatus includes a base 12 having an upper surface 14 that is planar, smooth, and level for supporting a stack of sheets S to be tested. The base can comprise a plate of metal or other suitable material. The base has width and length dimensions that exceed the width and length dimensions of the stack of sheets S. The thickness of the base is sufficient to impart enough bending stiffness to the base to maintain the desired planarity of the upper surface 14 under conditions of use. Typically, the testing apparatus can be supported on a suitably planar and level support surface such as the top of a work bench or the like.

The apparatus 10 further includes a weight 16 for placing atop the stack S of sheets. The weight 16 has a planar upper surface 18 and a planar lower surface 20 that is parallel to the upper surface 18. The weight can comprise a plate of a suitable material such as glass or transparent polymer; alternatively, the material can be an opaque or translucent material such as metal or non-transparent polymer. In one embodiment for use in testing 305 mm (12 inch) squares of paperboard material, the weight 16 comprises a glass plate having a thickness of about 6 mm (¼-inch), such as a thickness of 5.64 mm (0.222 inch), as measured between the upper surface 18 and the lower surface 20. The weight has a mass of about 61 g (about 0.135 lb). However, it will be appreciated that the particular dimensions and mass of the weight 16 generally will depend on the characteristics of the sheet material being tested.

The apparatus 10 also includes a measuring device such as a ruler 22 for measuring a height H of the stack S of sheets. The ruler 22 is affixed to the base 12 and extends vertically upward from the base adjacent one edge thereof. The ruler has a graduated scale 24 for measuring distance. The "zero" on the graduated scale 24 is at the same vertical level as the upper surface 14 of the base 12. Thus, the scale 24 allows an operator to determine a vertical distance D of the upper surface 18 of the weight 16 above the upper surface 14 of the base 12. This vertical distance D is equal to the height H of the stack plus the thickness of the weight 16. Therefore, the height H can be determined based on the measured distance D and the known thickness of the weight.

The apparatus 10 advantageously also can include vertical guide members 26 for guiding and aligning the weight 16 directly above the base 12 so that one edge of the weight is closely adjacent to the ruler 22. The guide members 26 are affixed to the base 12 adjacent its four corners and extend vertically upward therefrom. The guide members can comprise rods or cylinders (solid or hollow) of metal, plastic, or other suitable material. The weight 16 includes apertures 28 adjacent the corners thereof for receiving the guide members 26. The guide members 26 loosely fit in the apertures 28 to avoid any possibility of binding of the weight. The weight must be freely movable in the vertical direction so that the weight is entirely supported by the stack S of sheets.

FIG. 2 diagrammatically illustrates a stack S of sheets 30 of material to be tested, placed atop the upper surface 14 of the base 12, with the weight 16 then rested atop the stack. The sheets 30 are not perfectly flat, but have waviness, which is greatly exaggerated in FIG. 2 for clarity of illustration. To determine a quantitative measure of the waviness of the sheets, the height H of the stack is determined by noting the distance D of the upper surface 18 of the weight above the upper surface 14 of the base 12, using the ruler 22. The height H is equal to the distance D minus the thickness of the weight 16, as previously noted.

Next, a "Wavy Ratio" is computed as

Wavy Ratio=$H/(n \cdot t)$ where n is the number of sheets 30 (n=5 in the illustrated example), and t is the average caliper of the sheets. The average caliper t of sheet material is often specified by the manufacturer.

Standard procedures exist for measuring the caliper of paper materials. For example, TAPPI test method T 411 describes a procedure for measuring single-sheet thickness and variations in single-sheet thickness of paper, paperboard, and combined board. Another method for measuring the thickness of paper is TAPPI T 500 "Book Bulk and Bulking Number of Paper," which describes a procedure for measuring the overall thickness of a stack of book paper under a pressure of 250 kPa (35 psi). An essentially identical method is described in ASTM D 645-96.

Figure 3:
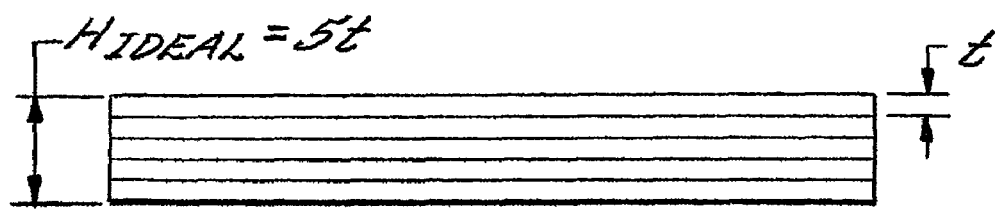
FIG. 3 is a front elevation of an "ideal" stack of sheets.

With reference to FIG. 3, it will be seen that the quantity (n·t) represents the "ideal height" of the stack of sheets if the sheets were all perfectly flat with no waviness. Thus, the Wavy Ratio represents the actual height divided by the ideal height, and hence is a quantity that always exceed unity by some amount. The amount by which the Wavy Ratio exceeds unity is a measure of the waviness of the sheets.

It will be recognized that the upper surface of the stack S of sheets in general will not be perfectly level, and hence the location of the upper surface (or upper datum plane) of the weight 16 on the ruler 22 actually represents the height of the stack at only one edge of the stack. Thus, if the stack were rotated about a vertical axis and the height were measured again, in general the second measurement would not be equal to the first measurement. Accordingly, the method in accordance with one embodiment of the invention attempts to take the varying stack height into account by taking a plurality of height measurements and averaging them. For example, a first measurement $H_1$ is taken with the stack S in a first rotational orientation. Advantageously, when the sheets comprise paper or paperboard, which has a "machine direction", all of the sheets are oriented with their machine direction in the same direction.

Next, the weight 16 is removed and the stack is rotated 180° about a vertical axis, the weight 16 is replaced, and a second height measurement $H_2$ is taken. The average of the two height measurements is then used as the height H in the above Wavy Ratio formula. The method is not limited to taking only two measurements. It is possible to take three measurements with the stack in three different orientations 90° apart, or even to take four measurements in four different orientations 90° apart, and average the measurements.

In using the apparatus 10, it generally will be more convenient to determine the distance D by noting the location of the weight's upper surface 18 on the ruler 22, as opposed to directly determining the height H by noting the location of the weight's lower surface 20 on the ruler. Accordingly, an operator using the apparatus can record a first distance $D_1$ with the stack in a first orientation, and then can rotate the stack and record a second distance $D_2$. The Wavy Ratio then can be computed as Wavy Ratio=$[0.5 \cdot (D_1+D_2)-TW]/(n \cdot t)$, where TW is the thickness of the weight 16.

It is also possible to position the ruler 22 so that the "zero" mark of the scale 24 is offset upward relative to the upper surface 14 of the base 12 by an amount equal to the thickness of the weight 16. In this manner, the location of the upper surface 18 of the weight on the ruler 22 will be a direct indication of the height H of the stack. However, the drawback of this approach is that the ruler must be repositioned if the weight is replaced by one of different thickness.

To assist the operator in making the calculation of Wavy Ratio according to the above formula, the apparatus 10 can include a microprocessor 40 connected to an input device 50 such as a keypad or the like. The microprocessor 40 is programmed to compute the Wavy Ratio from the above formula based on inputs $D_1$ and $D_2$ and the known values TW, n, and t, which are stored in memory associated with the microprocessor. The computed Wavy Ratio is then displayed on a display device 60 connected with the microprocessor. The microprocessor can also be programmed to tabulate, graph, and/or perform data analysis on a plurality of Wavy Ratio measurements for a plurality of tests, and the results of the analyses can be displayed on the display device as data listings, graphs, charts, or the like.

Various other modifications to the apparatus and/or method can be made. For example, rather than deriving the ideal stack height by the calculation (n·t), it is possible to measure an ideal stack height by adding a heavy weight atop the weight 16 (or by replacing the weight 16 with one of substantially greater weight) so as to compress the stack of sheets and thereby take out most or all of the waviness of the sheets. In this approach, one height measurement would be taken with a light weight and a second measurement would be taken with a heavy weight, and a Wavy Ratio would be computed as $$\text{Wavy Ratio} = H_{light}/H_{heavy}.$$

Multiple measurements with different stack orientations can be used with this modified approach, similar to the procedure described above.

Figure 4:
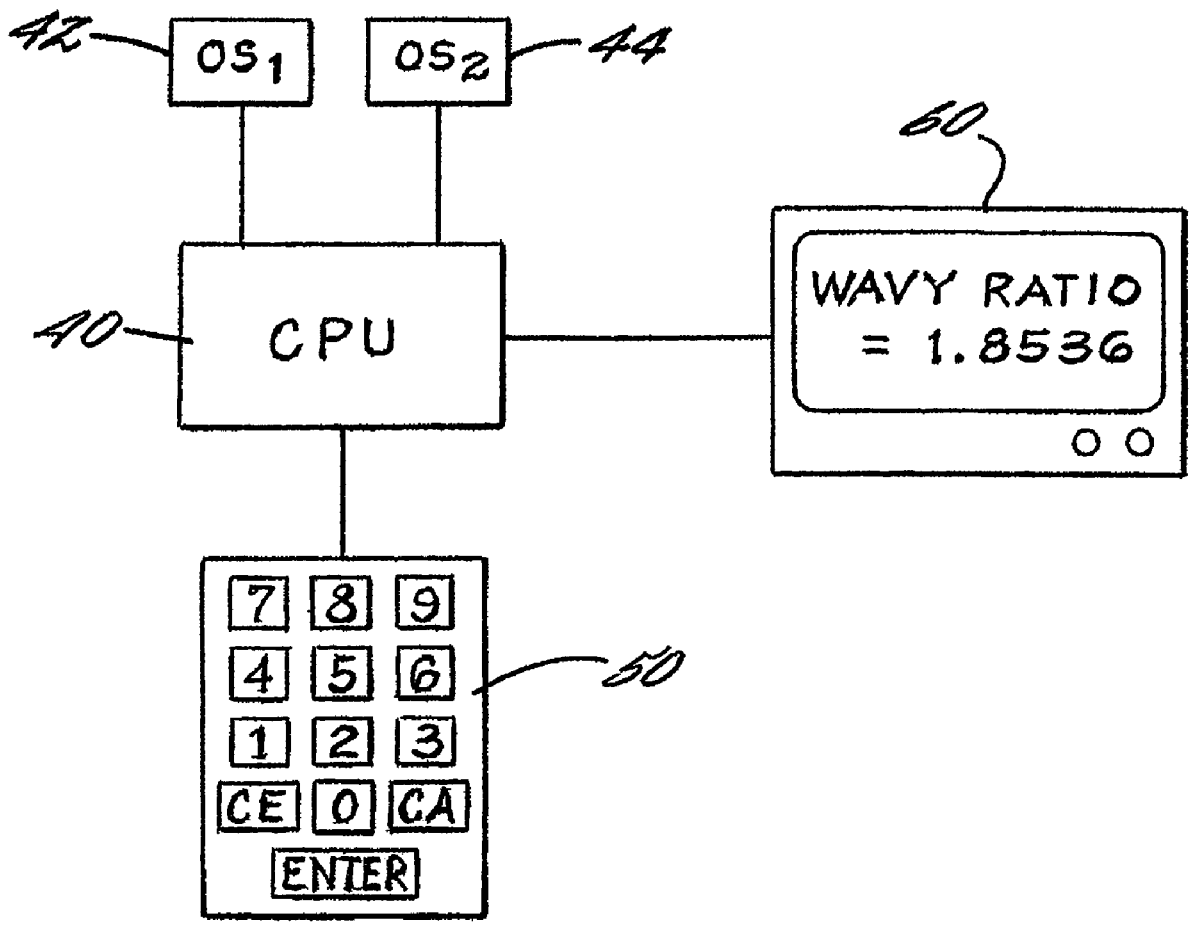
FIG. 4 is a diagrammatic illustration of a microprocessor, input device, and display device for use with the testing apparatus for computing a Wavy Ratio.

The apparatus 10 can be modified in various ways. For example, the weight 16 can have various configurations, as long as it presents a lower surface that is flat and contacts enough of the upper surface of the stack to exert a generally uniform pressure on the top of the stack. Additionally, various types of devices can be used for measuring the height of the stack. For instance, an optical sensor 42 (FIG. 4) can be attached to or integrated into the base 12 for measuring the height of the lower surface 20 of the weight 16 above the base. The sensor 42 can output a signal directly to the microprocessor 40 (e.g., in response to an operator pressing a button to initiate a height measurement) rather than an operator having to input the height using the keypad 50. This can eliminate input errors. It is furthermore possible to include two (or more) such optical sensors (e.g., see optical sensors 42, 44 in FIG. 4) for taking two (or more) height measurements to be averaged, thus eliminating the requirement to rotate the stack for multiple measurements.

As yet another modification, it is not essential to determine a Wavy Ratio for assessing waviness of the sheets. Alternatively, it is possible to determine an average "effective caliper" $t_{eff}$ of the sheets as $$t_{eff} = H/n.$$

The effective caliper is made greater by waviness. If all of the sheets were perfectly flat, then the average effective caliper would be equal to the average caliper. Thus, the extent by which the average effective caliper of the sheets exceeds the average caliper is an indication of the extent of waviness of the sheets.

In the embodiments described above, the height of the stack is not directly measured, but instead a height of a surface of the weight 16 is measured, which either directly corresponds to the stack height (when the height of the lower surface of the weight is measured), or differs from the stack height by the thickness of the weight (when the height of the upper surface of the weight is measured). Alternatively, however, it is possible to directly measure the height of the top surface of the stack above the base's upper surface 14. For example, one or more optical sensors can be arranged spaced above the base 12, pointing straight downward at the top surface of the stack, for measuring the stack height at one or more locations. The difficulty with this approach is that the weight 16 generally will interfere with the measurement if the weight covers the entire stop surface of the stack. Accordingly, the weight can be made smaller than the stack so that a peripheral region of the stack is not covered by the weight, and the optical sensor(s) can be aimed to detect the height in this peripheral region. Another drawback with this approach is that the waviness of the top sheet in the stack can skew the measurement. For example, if the location of the optical sensor happens to correspond to the crest of a wave, then an artificially high stack height may be measured, whereas an artificially low height may be measured if the optical sensor's location happens to be in a valley between two waves. This can be at least partially accounted for by taking height measurements at multiple locations and averaging the measurements as previously discussed. The use of a weight 16 and the measurement of a height of the weight tends to average out the waviness of the top sheet in a similar fashion.

In any of the various embodiments of the invention as described above, the results of the measurements can be used for quality control of the sheet material from which the sample sheets are taken. In general, the sample sheets should be selected from the manufacturing run or lot of sheet material in a manner designed to ensure that the samples are truly representative of the sheet characteristics of interest. For example, a web of paperboard made from recycled fibers with added starch tends to have ridges or waves that run in the machine direction and sometimes in the cross-machine direction of the web. It may be desirable to take multiple sets of sample sheets from various locations in the web. As an example, one set of five sample sheets can be taken from a portion of the paperboard web proximate one longitudinal edge of the web, a second set of five sample sheets can be taken from a portion of the web intermediate the longitudinal edges, a third set can be taken from a portion of the web proximate the other longitudinal edge, etc. In this example, the sheets of a given set are taken from locations spaced apart along the machine direction of the web. As another example, the sheets of each set can be taken from locations spaced apart along the cross-machine direction, and the various sets can be taken from locations spaced apart along the machine direction. Alternatively, the sheets in a given set can be taken from various locations randomly chosen, and/or the various sets can be from randomly chosen locations. Other sample selection methods can also be used.

When used as a quality control for sheet material, the method in accordance with the invention generally entails comparing an "actual" quantity (e.g., the height of a stack of sheets, or the average effective caliper of the sheets) with a corresponding "ideal" quantity (e.g., the ideal stack height, or the average caliper). A predetermined threshold is established for determining whether the sheets are acceptable or not. For example, when the Wavy Ratio is computed as the ratio of the actual stack height to the ideal stack height, a predetermined threshold value for the ratio is established. If the computed Wavy Ratio exceeds the predetermined threshold value, then the sheet material is rejected; if the Wavy Ratio does not exceed the threshold value, then the sheet material is accepted (at least in terms of waviness—other characteristics of the sheet material assessed by other quality control tests could still be unacceptable). The particular value of the threshold Wavy Ratio will generally depend on various factors such as the type of sheet material being tested, the application for which the sheet material is intended, the needs of the particular customer for the sheet material, etc.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for measuring waviness of sheet materials, comprising:
    a base having a horizontal planar upper surface for supporting a stack of sheets thereon;
    a weight that rests freely atop an uppermost sheet of the stack; and
    a measuring device for measuring a vertical distance between an upper datum plane corresponding to a top surface of the stack and a lower datum plane corresponding to a lower surface of the stack, the vertical distance being indicative of a height H of the stack.

2. The apparatus of claim 1, further comprising a microprocessor, an input device connected to the microprocessor, and a display device connected to the microprocessor, the microprocessor being programmed to calculate a Wavy Ratio as $$\text{Wavy Ratio} = H/(n \cdot t)$$

where n is the number of sheets in the stack and t is an average caliper of the sheets, and to display the calculated Wavy Ratio on the display device.

3. The apparatus of claim 1, wherein the measuring device comprises a ruler extending vertically above the base.

4. The apparatus of claim 3, further comprising a guide arrangement for guiding and aligning the weight with respect to the ruler.

5. The apparatus of claim 4, wherein the guide arrangement comprises a vertical guide member engaging the weight.

6. The apparatus of claim 5, wherein the vertical guide member extends through an aperture in the weight.

7. The apparatus of claim 5, wherein the guide arrangement comprises a plurality of horizontally spaced vertical guide members extending through respective apertures in the weight.

8. The apparatus of claim 7, wherein the weight comprises a plate that is generally rectangular or square having four corners and having four apertures located adjacent the corners, and wherein there are four vertical guide members each extending through one of the apertures.

9. The apparatus of claim 1, wherein the measuring device comprises an optical sensor operable for measuring the height H of the stack.

10. The apparatus of claim 9, further comprising a microprocessor connected with the optical sensor, the microprocessor being programmed to perform calculations based on the height measured by the optical sensor.

11. The apparatus of claim 10, wherein there are a plurality of optical sensors operable for measuring a height of the stack at different locations, and wherein the microprocessor is programmed to average the heights measured by the optical sensors.

12. The apparatus of claim 1, wherein the base and the plate are generally rectangular or square plates each having length and width dimensions, and wherein the dimensions of the weight are substantially equal to those of the base.

13. A method of quality control for a sheet material, comprising the steps of:
    stacking a plurality n of sheets of the sheet material one upon another on a horizontal planar upper surface of a base to form a stack, the sheets having an average caliper t, the number n of sheets being known;
    determining a height H of the stack by resting a weight freely atop the stack and measuring a vertical distance between an upper datum plane corresponding to a top surface of the stack and a lower datum plane corresponding to a lower surface of the stack; and
    comparing the height H with an ideal height that a stack of n sheets would have in the absence of waviness, so as to assess how much waviness the sheets have.

14. A method of quality control for a sheet material, comprising the steps of:
    stacking a plurality n of sheets of the sheet material one upon another to form a stack, the sheets having an average caliper t, the number n of sheets being known;
    determining a height H of the stack;
    computing a Wavy Ratio as $$\text{Wavy Ratio} = H/(n \cdot t); \text{ and}$$

comparing the Wavy Ratio to a predetermined threshold value and rejecting the sheet material if the Wavy Ratio exceeds the threshold value.

15. The method of claim 13, wherein the sheet material comprises paper, each sheet having a machine direction, and wherein the sheets are stacked all having the machine direction oriented in the same direction.

16. A method of quality control for aسheet material, comprising the steps of:
    stacking a plurality n of sheets of the sheet material one upon another to form a stack, the sheets having an average caliper t, the number n of sheets being known;
    determining a height H of the stack; and
    comparing the height H with an ideal height that a stack of n sheets would have in the absence of waviness, so as to assess how much waviness the sheets have, wherein the height H is based on an average of a plurality of measurements taken with the stack in a plurality of different rotational orientations about a vertical axis.

17. The method of claim 16, wherein the height H is based on an average of two measurements taken with the stack rotated 180 degrees about the vertical axis relative to each other.

18. A method of quality control for a sheet material, comprising the steps of:
    stacking a plurality n of sheets of the sheet material one upon another to form a stack, the sheets having an average caliper t;
    determining a height H of the stack;
    computing an average effective caliper $t_{\mathit{eff}}$ of the sheets as $$t_{\mathit{eff}} = H/n; \text{ and}$$

comparing the average effective caliper $t_{\mathit{eff}}$ to the average caliper t of the sheets and rejecting the sheet material if the average effective caliper $t_{\mathit{eff}}$ exceeds the average caliper t by more than a predetermined threshold amount.

* * * * *